United States Patent
Fitos

(10) Patent No.: US 8,776,263 B1
(45) Date of Patent: Jul. 15, 2014

(54) WELDING MASK SYSTEM

(76) Inventor: Anastasios Fitos, Palm Harbor, FL (US)

(*) Notice: Subject to any disclaimer, the term of this patent is extended or adjusted under 35 U.S.C. 154(b) by 0 days.

(21) Appl. No.: 13/484,779

(22) Filed: May 31, 2012

(51) Int. Cl.
*A61F 9/06* (2006.01)

(52) U.S. Cl.
USPC .................................. 2/8.3; 2/8.4

(58) Field of Classification Search
USPC ............................... 2/8.1–8.4, 8.7
See application file for complete search history.

(56) References Cited

U.S. PATENT DOCUMENTS

| | | | | |
|---|---|---|---|---|
| 1,416,848 A * | 5/1922 | Lightfield | | 2/8.2 |
| 1,877,024 A * | 9/1932 | Norton | | 2/8.3 |
| 1,905,210 A * | 4/1933 | Bowers | | 2/8.2 |
| 2,017,059 A * | 10/1935 | Gingg | | 2/8.7 |
| 2,056,027 A * | 9/1936 | Tracey | | 2/8.7 |
| 2,152,383 A * | 3/1939 | Leader | | 2/8.2 |
| 2,263,116 A * | 11/1941 | Andrews | | 2/8.7 |
| 2,411,224 A * | 11/1946 | O'Reilly | | 2/8.3 |
| 2,417,883 A * | 3/1947 | Oschin | | 219/147 |
| 3,086,213 A * | 4/1963 | Crozat et al. | | 2/8.3 |
| 3,159,844 A * | 12/1964 | Haboush | | 2/8.4 |
| 3,332,087 A * | 7/1967 | Manz | | 2/8.3 |
| 3,601,814 A * | 8/1971 | Manz | | 2/8.3 |
| 3,768,099 A * | 10/1973 | Manz | | 2/8.3 |
| 3,943,573 A * | 3/1976 | Budmiger | | 2/8.3 |
| 4,039,254 A * | 8/1977 | Harsch | | 349/14 |
| 4,071,912 A * | 2/1978 | Budmiger | | 2/8.8 |
| 4,193,132 A * | 3/1980 | Peterson | | 2/8.1 |
| 4,853,973 A * | 8/1989 | Boochard | | 2/8.1 |
| 5,224,219 A * | 7/1993 | Edwards et al. | | 2/8.3 |
| 2004/0177426 A1* | 9/2004 | Wang-Lee | | 2/63 |
| 2007/0089216 A1* | 4/2007 | Walkden | | 2/8.7 |

* cited by examiner

*Primary Examiner* — Richale Quinn

(57) ABSTRACT

A face plate has a major chamber positionable in front of a face of a welder. A visor housing has a forward opening. A minor chamber is provided within the visor housing. A forward assembly is fixedly positioned within the minor chamber adjacent to the forward opening. The forward assembly has a glass ultraviolet filter centrally. The forward assembly has a heat resistant transparent plate outwardly. The forward assembly has a fixed polarized filter lens inwardly. A rearward assembly is fixedly positioned within the major chamber adjacent to the visor housing. The rearward assembly includes a rotatable polarized filter lens. A drive assembly is adapted to rotate the rotatable polarized filter lens with respect to the fixed polarized filter lens.

1 Claim, 3 Drawing Sheets

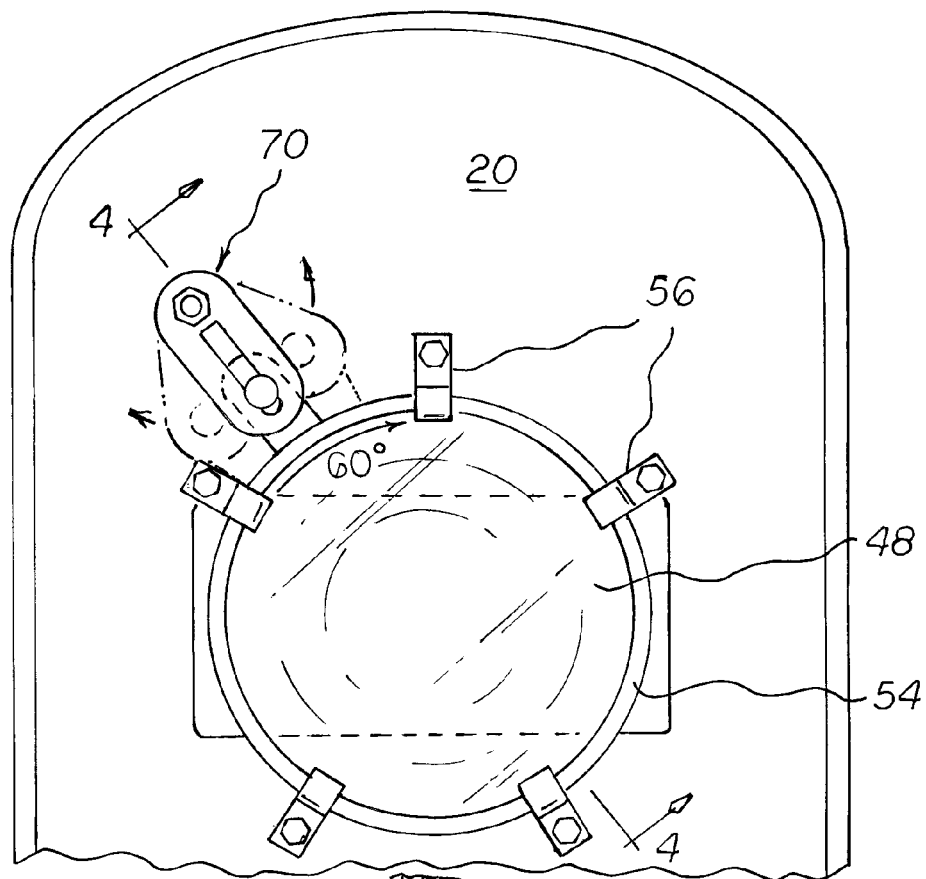
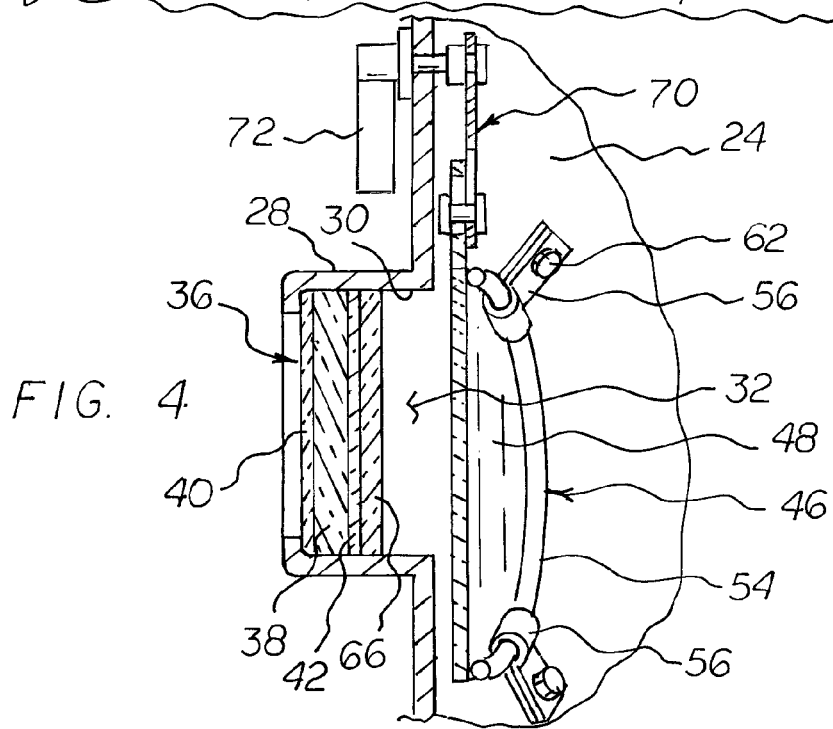

WELDING MASK SYSTEM

BACKGROUND OF THE INVENTION

Field of the Invention

The present invention relates to a welding mask system and more particularly pertains to protecting a welder's face from heat and sparks, the system also including a visor for protecting the welder's eyes from light at the discretion of the welder, the protection of the welder's face and the protection of the welder's eyes being done in a safe, convenient and economic manner.

SUMMARY OF THE INVENTION

In view of the disadvantages inherent in the known types of mask systems of known designs and configurations now present in the prior art, the present invention provides an improved welding mask system. As such, the general purpose of the present invention, which will be described subsequently in greater detail, is to provide a new and improved welding mask system and method which has all the advantages of the prior art and none of the disadvantages.

To attain this, the present invention essentially comprises a welding mask system. A face plate has a major chamber positionable in front of a face of a welder. A visor housing has a forward opening. A minor chamber is provided within the visor housing. A forward assembly is fixedly positioned within the minor chamber adjacent to the forward opening. The forward assembly has a glass ultraviolet filter centrally. The forward assembly has a heat resistant transparent plate outwardly. The forward assembly has a fixed polarized filter lens inwardly. A rearward assembly is fixedly positioned within the major chamber adjacent to the visor housing. The rearward assembly includes a rotatable polarized filter lens. A drive assembly is adapted to rotate the rotatable polarized filter lens with respect to the fixed polarized filter lens.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved welding mask system which has all of the advantages of the prior art mask systems of known designs and configurations and none of the disadvantages.

It is another object of the present invention to provide a new and improved welding mask system which may be easily and efficiently manufactured and marketed.

It is further object of the present invention to provide a new and improved welding mask system which is of durable and reliable constructions.

An even further object of the present invention is to provide a new and improved welding mask system which is susceptible of a low cost of manufacture with regard to both materials and labor, and which accordingly is then susceptible of low prices of sale to the consuming public, thereby making such welding mask system economically available to the buying public.

Even still another object of the present invention is to provide a welding mask system for protecting a welder's face from heat and sparks, the system also including a visor for protecting the welder's eyes from light at the discretion of the welder, the protection of the welder's face and the protection of the welder's eyes being done in a safe, convenient and economic manner.

Lastly, it is an object of the present invention to provide a new and improved welding mask system. A face plate has a major chamber positionable in front of a face of a welder. A visor housing has a forward opening. A minor chamber is provided within the visor housing. A forward assembly is fixedly positioned within the minor chamber adjacent to the forward opening. The forward assembly has a glass ultraviolet filter centrally. The forward assembly has a heat resistant transparent plate outwardly. The forward assembly has a fixed polarized filter lens inwardly. A rearward assembly is fixedly positioned within the major chamber adjacent to the visor housing. The rearward assembly includes a rotatable polarized filter lens. A drive assembly is adapted to rotate the rotatable polarized filter lens with respect to the fixed polarized filter lens.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a cross sectional view taken along line 3-3 of FIG. 2.

FIG. 4 is a cross sectional view taken along line 4-4 of FIG. 3.

The same reference numerals refer to the same parts throughout the various Figures.

DESCRIPTION OF THE PREFERRED EMBODIMENT

Figure 1:
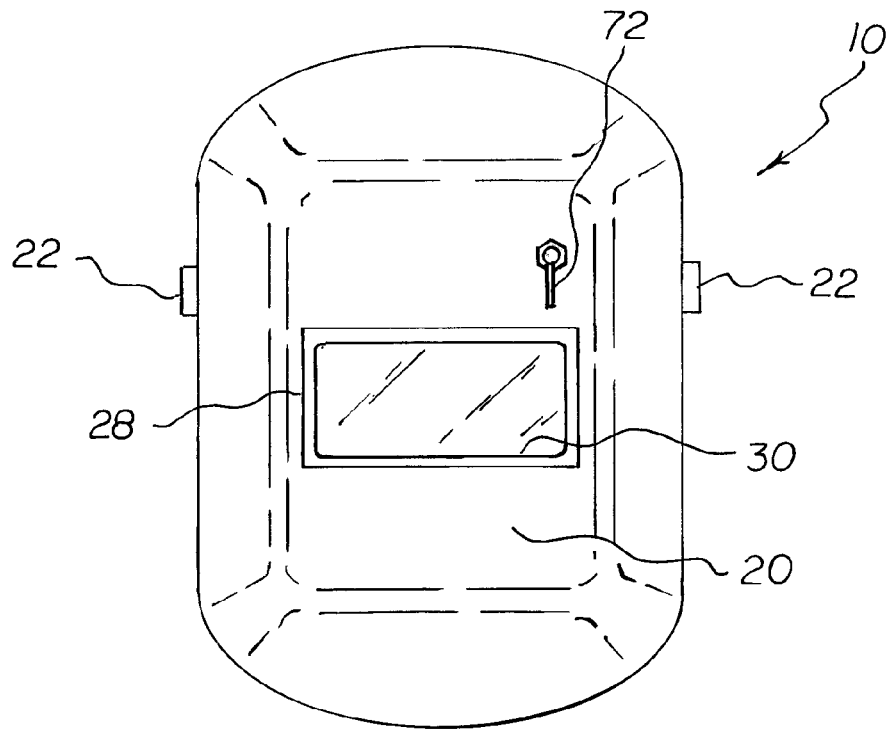
FIG. 1 is a front elevational view of a welding mask system constructed in accordance the principles of the present invention.
Figure 2:
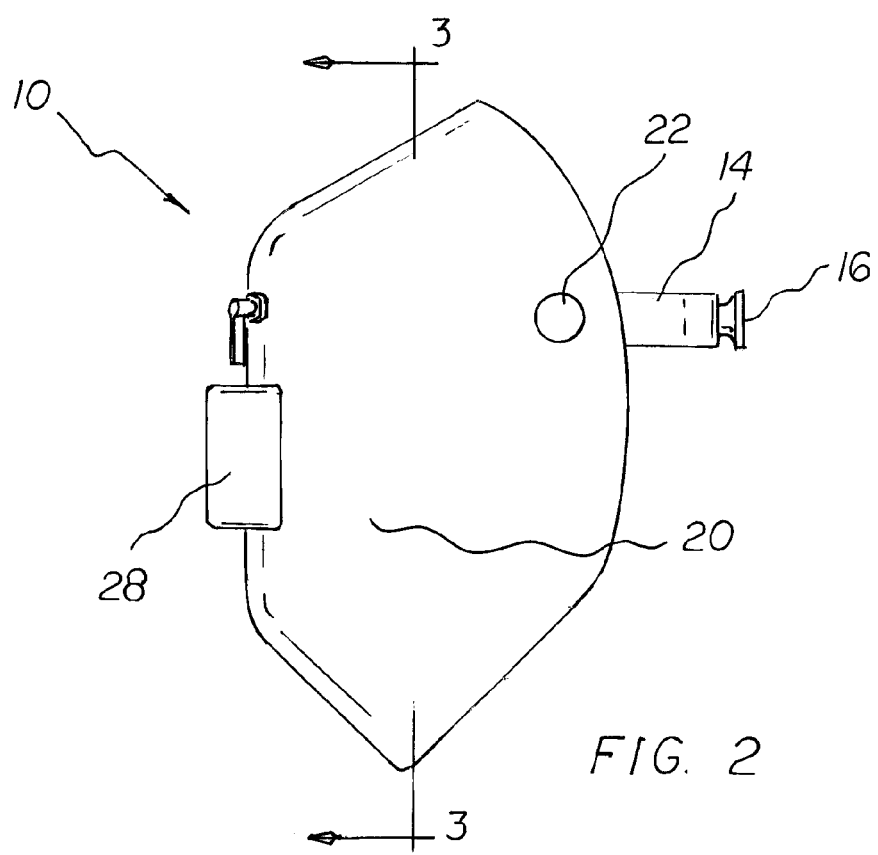
FIG. 2 is a side elevational view of the welding mask system of FIG. 1.

With reference now to the drawings, and in particular to FIG. 1 thereof, the preferred embodiment of the new and improved welding mask system embodying the principles and concepts of the present invention and generally designated by the reference numeral 10 will be described.

The present invention, the welding mask system 10 is comprised of a plurality of components. Such components in their broadest context include a face plate, a visor housing, a forward assembly, a rearward assembly, and a drive assembly. Such components are individually configured and correlated with respect to each other so as to attain the desired objective.

First provided is a head band 14. The head band is postionable around a head of a welder above a wearer's eyes and ears. The head band has adjustment mechanisms 16. The adjustment mechanisms are operable under the control of the welder. In this manner the size of the head band is adjustable to suit the size of the welder's head. The head band is fabricated of a flexible material.

A face plate 20 is provided. The face plate is positionable in front of a face of the welder. The face plate has an interior surface and an exterior surface. The face plate is fabricated of a rigid material. A pair of pivot bolts 22 is provided. The bolts pivotably couple the face plate to the head band. In this manner the face plate is movable between lowered operative position and a raised inoperative position. In the operative position, the face plate is provided in front of the face of the welder. In the inoperative position, the face plate is provided above the face of the welder. The face plate has a major chamber 24. The major chamber is provided within the face plate. In this manner the face of the welder is received when in the operative position.

A visor housing 28 is provided. The visor housing is formed in a central extent of the face plate. The visor housing extends forwardly of eyes of the welder. The visor housing has a forward opening 30. The forward opening is in a rectangular configuration. The visor housing has a minor chamber 32. The minor chamber is provided within the visor housing.

A forward assembly 36 is provided. The forward assembly is fixedly positioned within the minor chamber adjacent to the rectangular opening. The forward assembly includes a glass or plastic ultraviolet filter 38. The ultraviolet filter is in a configuration, rectangular or square or round or the like. The ultraviolet filter has a thickness of 0.250 inches. The forward assembly also includes an outer transparent plate 40. The outer transparent plate is fabricated of a heat resistant plastic. The outer transparent plate has a thickness of 0.035 inches. The forward assembly also includes an inner fixed polarized filter lens 42. The fixed polarized filter lens has etched parallel grating lines. Each inch includes about 10,000 and 20,000 lines. In this manner the wavelength of light passing through the lens may be varied. The fixed polarized filter lens has a thickness of 0.035 inches.

A rearward assembly 46 is provided next. The rearward assembly is fixedly positioned within the major chamber adjacent to the visor housing. The rearward assembly includes a rotatable polarized filter lens 48. The rotatable polarized filter lens has etched parallel grating lines. Each inch includes about 10,000 and 20,000 lines. In this manner the wavelength of light passing through the lens may be varied. The rotatable polarized filter lens is generally circular in configuration. The rotatable polarized filter lens has a periphery. The lens has a radial tab 50. The radial tab has a radial slot 52. The rearward assembly includes a retaining ring 54. The retaining ring is attached to the periphery of the each clip. Each clip has a cylindrical section. In this manner the cylindrical section slidably receives a section of the retaining ring. A plurality of clips 56 is provided. Each clip has a cylindrical section 58. In this manner the cylindrical section slidably receives a section of the retaining ring. Each clip has an apertured section 60. Each clip has a fastener 62. In this manner the ring and the rotatable polarized filter lens are secured in the major chamber to overlie the minor chamber.

Further provided is an optical magnification lens 66. The optical magnification lens has a rectangular periphery. The optical magnification lens is fixedly positioned inwardly of the polarizing lens.

Provided last is a drive assembly 70. The drive assembly is adapted to rotate the rotatable polarized filter lens with respect to the fixed polarized filter lens. The drive assembly includes an operator controlled lever 72. The lever extends outwardly from the exterior surface of the face plate above the visor housing. The lever is illustrated as preferably positioned adjacent to the right side of the visor housing for right handed welders, but it should be appreciated that the lever is adapted for positioning on the left side for left handed welders. A pivot pin 74 is provided. The pivot pin extends through the face plate. The pivot pin has an interior end. The pivot pin has an exterior end. The exterior end is attached to the lever. A link 76 is provided. The link has an aperture above. The aperture is attached to the interior end of the pivot pin. The link has a slot 78 below. The link overlies the slot of the lens tab. A slide pin 80 is provided. The slide pin extends through the slots of the link and the lens tab. In this manner rotation of the lever will rotate the rotatable polarized filter lens with respect to the fixed polarized filter lens. Also in this manner the etched parallel grating lines may be varied. Further in this manner the light passing through the lenses may be increased or decreased.

Figure 5:
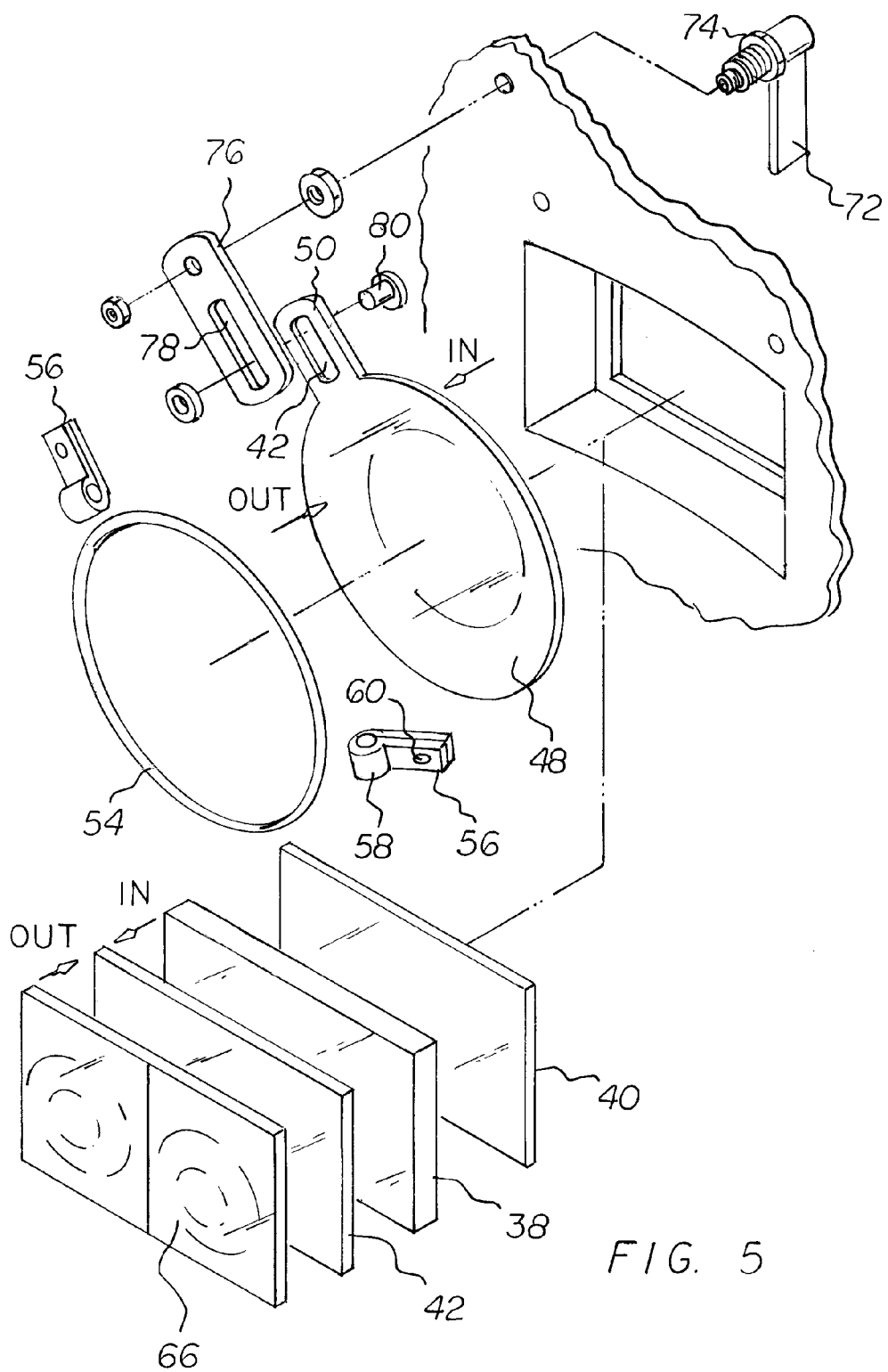
FIG. 5 is an exploded perspective illustration from interior of the system.

This invention allows the user to manually change the amount of light that comes through the filters as illustrated in FIG. 5, Ref No. 58 either a plastic, or glass filter, which itself can have a difference of shades from No. 3 to No. 10, No. 3 being the lightest and No. 10 the darkest. Best choice of shade for that filter is from No. 3 to No. 7 since any other choice would make it too dark. This filter would be changed at will. Thus, a two-way system is achieved for the welder to make a choice for the amount of light that passes through the three filters in FIG. 5. The stationary filters 38 and 42 are polarized filters. A filter 48 is also polarized and is adjustable with lever handle 72.

The moving polarized filter 48 is phased with the stationary polarized filter No. 42 so that it travels from 0 degrees to 60 degrees. These two filters must be marked as shown in FIG. 5 with IN and OUT when cutting filters out for manufacturing.

In FIG. 5, a thermoplastic cover 40 protects the other filters from hot weld splash. The system of the present invention does not require any batteries, nor complicated electronics, for darkening the mask light inlet, thereby avoiding the possibility of destroying the electronics from either hot weld splashes or humid conditions which may destroy the contacts. The lithium batteries used in the prior art leach out chemicals that are very corrosive and very toxic, especially to the welder who is breathing in these fumes. Under working conditions, a cherry red hot rod touching the inside mask causes irreparable damage.

The present invention design of mask is superior to the prior art in adverse conditions, such as if a hot rod accident occurred. In this event, a piece of aluminum tape could be placed over the damaged area and work could be completed.

Thereafter, the lens could be replaced. Accordingly, this system has superior advantages over the prior art systems using electronics.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A welding mask system (10) including a face plate for protecting a welder's face from heat and sparks, the system also including a visor for protecting the welder's eyes from light at the discretion of the welder, the protection of the welder's face and the protection of the welder's eyes being done in a safe, convenient and economic manner, the system comprising, in combination:

a head band (14) positionable around a head of a welder above a wearer's eyes and ears, the head band having adjustment mechanisms (16) operable under the control of the welder for adjusting the size of the head band to suit the size of the welder's head, the head band being fabricated of a flexible material;

a face plate (20) positionable in front of a face of the welder, the face plate having an interior surface and an exterior surface, the face plate being fabricated of a rigid material, a pair of pivot bolts (22) pivotably coupling the face plate to the head band for movement of the face plate between lowered operative position and a raised inoperative position, the operative position being in front of the face of the welder, the inoperative position being above the face of the welder, a major chamber (24) within the face plate for receiving the face of the welder when in the operative position;

a visor housing (28) formed in a central extent of the face plate, the visor housing extending forwardly of eyes of the welder, the visor housing having a forward opening (30) in a rectangular configuration, a minor chamber (32) within the visor housing;

a forward assembly (36) fixedly positioned within the minor chamber adjacent to the rectangular opening, the forward assembly including a glass ultraviolet filter (38), the ultraviolet filter being in a rectangular configuration with a thickness of 0.250 inches, the forward assembly also including an outer transparent plate (40) fabricated of a heat resistant plastic, the outer transparent plate having a thickness of 0.035 inches, the forward assembly also including an inner fixed polarized filter lens (42) with etched parallel grating lines between about 10,000 and 20,000 lines per inch for varying the wavelength of light passing there through, the fixed polarized filter lens having a thickness of 0.035 inches;

a rearward assembly (46) fixedly positioned within the major chamber adjacent to the visor housing, the rearward assembly including a rotatable polarized filter lens (48) with etched parallel grating lines between about 10,000 and 20,000 lines per inch for varying the wavelength of light passing there through, the rotatable polarized filter lens being generally circular in configuration with a periphery, the lens having a radial tab (50) with a radial slot (52), the rearward assembly including a retaining ring (54) attached to the periphery of the each clip having a cylindrical section slidably receiving a section of the retaining ring, a plurality of clips (56), each clip having a cylindrical section (58) slidably receiving a section of the retaining ring, each clip having an apertured section (60) with a fastener (62) to secure the ring and the rotatable polarized filter lens in the major chamber to overlie the minor chamber;

an optical magnification lens (66) having a rectangular periphery, the optical magnification lens being fixedly positioned inwardly of the polarizing lens; and a drive assembly (70) adapted to rotate the rotatable polarized filter lens with respect to the fixed polarized filter lens, the drive assembly including an operator controlled lever (72) extending outwardly from the exterior surface of the face plate above the visor housing, a pivot pin (74) extending through the face plate with an interior end and with an exterior end attached to the lever, a link (76) formed with an aperture above attached to the interior end of the pivot pin, the link formed with a slot (78) below overlying the slot of the lens tab, a slide pin (80) extending through the slots of the link and the lens tab whereby rotation of the lever will rotate the rotatable polarized filter lens with respect to the fixed polarized filter lens to vary the etched parallel grating lines and thereby increase and decrease the light passing through the lenses.

\* \* \* \* \*